United States Patent
Ou et al.

(10) Patent No.: US 10,533,074 B2
(45) Date of Patent: *Jan. 14, 2020

(54) SILICONE COMPOSITIONS RAPIDLY CROSS-LINKABLE AT AMBIENT TEMPERATURES AND METHODS OF MAKING AND USING SAME

(71) Applicant: Ethicon, Inc., Somerville, NJ (US)

(72) Inventors: Duan Li Ou, Warren, NJ (US); Leo B. Kriksunov, Ithaca, NJ (US); Lamar Kirchhevel, Laguna Hills, CA (US); Clifford Dwyer, Weston, FL (US)

(73) Assignee: ETHICON, INC., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/395,724

(22) Filed: Dec. 30, 2016

(65) Prior Publication Data

US 2018/0186938 A1  Jul. 5, 2018

(51) Int. Cl.
| | |
|---|---|
| *A61F 2/12* | (2006.01) |
| *A61M 5/00* | (2006.01) |
| *A61M 5/19* | (2006.01) |
| *A61M 5/24* | (2006.01) |
| *A61M 5/31* | (2006.01) |
| *A61M 5/32* | (2006.01) |
| *C08K 5/56* | (2006.01) |
| *A61L 27/18* | (2006.01) |
| *A61L 27/52* | (2006.01) |
| *C08G 77/12* | (2006.01) |
| *C08G 77/20* | (2006.01) |
| *C08G 77/38* | (2006.01) |
| *C08L 83/00* | (2006.01) |
| *C08L 83/04* | (2006.01) |

(52) U.S. Cl.
CPC ............... *C08G 77/20* (2013.01); *A61F 2/12* (2013.01); *A61L 27/18* (2013.01); *A61L 27/52* (2013.01); *A61M 5/002* (2013.01); *A61M 5/19* (2013.01); *A61M 5/2448* (2013.01); *A61M 5/3294* (2013.01); *C08G 77/38* (2013.01); *A61L 2400/06* (2013.01); *A61M 2005/3114* (2013.01); *A61M 2210/1007* (2013.01)

(58) Field of Classification Search
CPC ........ A61F 2/12; A61L 2400/06; A61L 27/56; A61M 2005/3114; A61M 2210/1007; C08G 77/08; C08J 2201/026
See application file for complete search history.

(56) References Cited

U.S. PATENT DOCUMENTS

| | | |
|---|---|---|
| 3,775,452 A | 11/1973 | Karstedt |
| 3,784,391 A | 1/1974 | Kruse et al. |
| 5,487,390 A | 1/1996 | Cohen et al. |
| 5,830,951 A | 11/1998 | Fiedler |
| 6,486,237 B1 | 11/2002 | Howe et al. |
| 6,622,633 B1 | 9/2003 | Johnsen et al. |
| 7,081,136 B1 | 7/2006 | Becker |

OTHER PUBLICATIONS

International Search Report & Written Opinion of the International Searching Authority issued in International Application No. PCT/US2017/063996 dated Mar. 20, 2018.

*Primary Examiner* — Stella K Yi
(74) *Attorney, Agent, or Firm* — Roberts Mlotkowski Safran Cole & Calderon P.C.

(57) ABSTRACT

Provided are rapidly cross-linkable silicone compositions, systems, kits, and methods for filling implanted medical devices in situ, the implanted medical devices, including for example, body implants and tissue expanders, the compositions including a platinum divinyl disiloxane complex; a low viscosity vinyl terminated polydimethylsiloxane; a low viscosity hydride terminated polydimethylsiloxane; and a silicone cross-linker, where the rapidly cross-linkable silicone composition has a viscosity of ≤150 cPs for ≥1 min. post-preparation and ≤300 cPs≤5 min. post-preparation, at ambient temperature.

15 Claims, No Drawings

SILICONE COMPOSITIONS RAPIDLY CROSS-LINKABLE AT AMBIENT TEMPERATURES AND METHODS OF MAKING AND USING SAME

FIELD

The present disclosure relates generally to silicone fluid compositions for use in implanted devices.

BACKGROUND

Currently, breast implants are filled with a regular, thermally cured silicone gel, and then implanted into a patient. The volume of silicone contained in a silicone filled implanted device, cannot be adjusted post-implant. Further, already implanted devices cannot be filled with a silicone gel after surgical implantation because current silicone gel formulations are highly viscous, for example, having a viscosity of >1000 cPs; thus they are not injectable via a hypodermic needle. In addition, currently used silicone gel formulations require thermal curing which cannot be carried out with regard to an already implanted device, or a device that is in the process of being surgically implanted or just before surgical implantation.

SUMMARY

The presently described subject matter is directed to a two-part, rapidly cross-linkable silicone (hereinafter "RCS") composition, comprising or consisting of a catalyst fluid comprising a first low viscosity vinyl terminated polydimethylsiloxane present in an amount of from about 97 wt % to about 99.5 wt % based on the weight of the catalyst fluid and having a viscosity of from about 1 to about 150 cPs, and a platinum divinyl disiloxane complex comprising $Pt[(CH_2=CH)(CH_3)_2SiOSi(CH_3)_2(CH=CH_2)]_3$, having a platinum (Pt) content of from about 2 to about 32 ppm based on the catalyst fluid, where the catalyst fluid has a viscosity of from about 1 to about 150 cPs; and a cross-linker fluid comprising a second low viscosity vinyl terminated polydimethylsiloxane present in an amount of from about 1 wt % to about 40 wt % based on the weight of the cross-linker fluid and having a viscosity of from about 1 to about 150 cPs, a low viscosity hydride terminated polydimethylsiloxane present in an amount of from about 60 wt % to about 90 wt % based on the weight of the cross-linker fluid and having a viscosity of from about 1 to about 150 cPs, and a silicone cross-linker comprising polymethylhydrosiloxane polydimethylsiloxane copolymer present in an amount of from about 0.32 wt % to about 5.0 wt % based on the weight of the cross-linker fluid, and having a viscosity of from about 1 to about 150 cPs, where the cross-linker fluid has a viscosity of from about 1 to about 150 cPs, and post-preparation, the resultant RCS composition has a viscosity of ≤150 cPs for ≥1 min. post-preparation and ≤300 cPs≤5 min. post-preparation, at ambient temperature. The resultant RCS composition, post-mixing, can have a platinum (Pt) content of from about 1 to about 16 ppm.

The presently described subject matter is further directed to a kit comprising a two-part, RCS composition, according to the presently described subject matter, where the catalyst fluid is provided in a first container, and the cross-linker fluid is provided in a second container.

The presently described subject matter is directed to a method of filling an implanted medical device in situ, comprising: providing a RCS composition according to the presently described subject matter; mixing the catalyst fluid with the cross-linker fluid to produce an injectable composition having an initial viscosity of <150 cPs for at least about 1 min.; and within ≤5 min. of initiating mixing, and substantially simultaneous with mixing, injecting a predetermined volume of the injectable composition into the implanted medical device in situ, whereby the rapidly cross-linkable silicone composition substantially cross-links and gels in situ in an amount of time ≥5 min. to produce a filled implant comprising a homogeneous rapidly cross-linkable silicone gel, where the RCS gel can have a viscosity as described herein, post-injection at ambient temperature. The RCS gel can have a viscosity ≥200,000 cPs≥60 min., ≥200,000 cPs≤24 hrs., ≥200,000 cPs≤12 hrs., ≥200,000 cPs≤6 hrs., ≥200,000 cPs≤3 hrs., ≥50,000 cPs≤24 hrs., ≥50,000 cPs≥1 hr., ≥50,000 cPs≤1 hr. and ≤6 hrs., ≥50,000 cPs≥1 hr. and ≤12 hrs., post-preparation or post-mixing at ambient temperature.

The presently described subject matter is directed to a method of adjusting the volume of an implanted medical device in situ, comprising: providing a kit accordingly to the presently described subject matter; mixing the catalyst fluid with the cross-linker fluid to produce an injectable composition having an initial viscosity of <150 cPs for at least about 1 min.; and within ≤5 min. or within ≤10 min. of initiating mixing, and/or substantially simultaneous with mixing, injecting a predetermined volume of the injectable composition into the implanted medical device in situ, whereby the rapidly cross-linkable silicone composition substantially cross-links and gels in situ in an amount of time ≥5 min. or ≥5 min. to ≤10 min., or ≥10 min. to produce a filled implant comprising a homogeneous silicone gel, wherein the rapidly cross-linkable silicone gel has a viscosity ≥200,000 cPs≥60 min. post-injection at ambient temperature, and the volume of the implanted device has been adjusted. The implanted medical device can be a permanent implant or a non-permanent implant according to the presently described subject matter. The presently described RCS gel can have a viscosity ≥50,000 cPs≤24 post-injection at ambient temperature.

DETAILED DESCRIPTION

Definitions

Any concentration ranges, percentage range, or ratio range recited herein are to be understood to include concentrations, percentages or ratios of any integer within that range and fractions thereof, such as one tenth and one hundredth of an integer, unless otherwise indicated.

About. As used herein, "about" refers to a degree of deviation based on experimental error typical for the particular property identified. The latitude provided the term "about" will depend on the specific context and particular property and can be readily discerned by those skilled in the art. Further, unless otherwise stated, the term "about" shall expressly include "exactly."

Order of steps. It should also be understood that, unless clearly indicated to the contrary, in any methods claimed herein that include more than one step or act, the order of the steps or acts of the method is not necessarily limited to the order in which the steps or acts of the method are recited.

Ambient Temperature. As used herein, the term "ambient temperature" refers to the temperature of the immediate environment. Ambient temperature as used herein can refer to a temperature of from about 18° C. to about 40° C., including but limited to, from about 20° C. to about 35° C., 20° C. to about 30° C., 20° C. to about 26° C., about 21° C., about 22° C., about 23° C., about 24° C., or about 25° C.

Breast Implant. As used herein, the term "breast implant" refers to a prosthesis consisting of a gel-like or fluid material in a flexible shell, implanted behind or in place of a breast in reconstructive or cosmetic surgery. The flexible shell can comprise a polymeric or elastomeric shell, including for example, a silicone shell, including a silicone elastomeric shell. The gel-like material or fluid material can include, for example, silicone gel or isotonic saline. The shell can be a single- or double-walled shell, or can include one or more double-walled areas. Suitable breast implants can be of any profile and size, and can include MENTOR® breast implants including adjustable implants including MENTOR® SPECTRUM® implants including SILTEX® implants, and BECKER design implants. Suitable implants come in a range of sizes, generally from 80 to 1000 cubic centimeters (cc) or milliliters in volume, e.g., from about 80 to about 800 cc or mls.

Adjustable Breast Implant. As used herein, the phrase "adjustable breast implant" refers to a breast implant that can be adjusted for volume during the implantation procedure or after healing of surgery. An initially empty inner shell or envelope can be later fully or partially filled with gel to make the final size adjustment. Likewise, saline in an initially saline filled shell can be removed and replaced with the presently described RCS composition. The use of the presently described RCS composition as an adjustment medium provides a consistent feel with the initial implanted gel implant, e.g., a cured silicone gel implant. Such implants can include, but are not limited to, a MENTOR® Becker style implant having an outer shell having a volume that is filled to about 75% to 95% with a cured gel (e.g., a conventional silicone gel), and, for example, an empty inner shell or envelope that can be filled at the time of implantation or at a different time point after surgery, e.g., after healing or remission of swelling. Filling can be accomplished via a valve to close the inner shell from the body. More than one fill port could be used and provide targeted fill adjustment areas such as upper pole and lower pole fill zones. The inner envelope can be attached to a bottom portion of the outer envelope and can define a volume of about 5% to about 15% or about 5% to about 10% of the volume of the outer envelope and can be empty or filled with saline. The implant can also include a self-sealing valve and/or filling tube, and/or mini-reservoir for adjusting the size of the implant. Suitable adjustable implants include those described in U.S. Pat. No. 7,081,136 hereby incorporated by reference in its entirety herein.

The terms "shell" and "envelope" are used interchangeably herein. Suitable implanted devices can include an elastomeric shell or envelope, including for example, but not limited to a silicone shell or envelope. A shell or envelope can comprise a double-walled shell or envelope, and/or a shell or envelope can comprise one or more double-walled areas.

Cure. As used herein, the term "cure" refers to a silicone polymer that has ceased to flow and has a viscosity above the limit of a Brookfield viscometer. The present RCS compositions can cure ≤12 hrs, ≤24 hrs, from 6 hrs to 24 hrs, from 12 hrs to 24 hrs, or about 24 hours. The present RCS compositions can be fully cured in about 24 hrs. The presently described RCS gels can have a viscosity of ≥200,000 cPs≥60 min., ≥200,000 cPs≥6 hrs., ≥200,000 cPs≥12 hrs., ≥200,000 cPs≥24 hrs., ≥50,000 cPs≥60 min., ≥50,000 cPs≥6 hrs., ≥50,000 cPs≥12 hrs., or ≥50,000 cPs≤24 hrs.

Flowable. As used herein, the term "flowable" refers to the ability of a material to run smoothly with unbroken continuity through a standard hypodermic needle, for example, through a standard gauge hypodermic syringe. Suitable needles include but are not limited to 18 to 21 gauge needles.

Implanted Medical Device. As used herein, the term "implanted medical device" refers to any flexible medical device that is implanted in an animal or for implantation in an animal, including but not limited to a human. Such devices can include permanent or non-permanent implanted medical devices. Suitable permanent body implants can include but are not limited to breast implants, adjustable breast implants, lumpectomy implants, calf implants, tissue expanders, and any other body implant for use in aesthetic and/or reconstructive surgery. Suitable permanent tissue expanders can include, for example, breast tissue expanders and calf tissue expanders. Suitable non-permanent body implants can include non-permanent tissue expanders including for example, non-permanent breast tissue expanders and non-permanent calf tissue expanders. Implanted medical devices can comprise one or more of a fluid filled shell and an empty, unfilled shell. Suitable fluid filled shells can include a saline filled or a silicone, e.g., conventional thermally cured silicone gel, filled shell. Suitable implanted devices can include an elastomeric shell or envelope, including a silicone shell or envelope. Suitable implanted medical devices can include one or more valves or ports to allow for fluid addition or removal, for example, using a syringe. Such valves and/or ports can include self-sealing valves or ports. The presently described implanted medical devices do not comprise solid implants, for example, solid silicone implants.

In Situ. As used herein, the term "in situ" refers to cross-linking of the RCS composition substantially within an implant that had previously been implanted in a subjects body That is, the RCS composition substantially cross-links in its desired and optimal position, i.e., within the already implanted medical device.

Injection. As used herein, the term "injection" refers to the administration of the presently described RCS composition into an implant device. Injection may or may not be through a valve, and may or may not be via a port. Injection can be performed directly through a wall of an implant device comprising, for example, a polymeric or elastomeric wall, such as a silicone or a silicone elastomer wall. When injection is directly through the shell of an implanted device (i.e., not via a valve or port), rapid cross-linking of the silicone gel results in the rapid formation of a gel plug in the shell of the implanted device, at the site of injection (i.e., needle stick site), thereby preventing any potential leakage of the gel from the implant at the site of injection. Further, when adding a RCS composition to an implanted medical device containing thermally cured silicone, the RCS composition can be injected at a location behind a portion of existing gel inside the implanted device.

Lumpectomy Implant. As used herein, the term "lumpectomy implant" refers to a football shaped shell configured to fit into lumpectomy excision during implantation into a lumpectomy void, where the shell can be implanted unfilled and filled in situ with the presently described RCS composition, at the time of lumpectomy or as a later revision surgery. After injecting the RCS composition into the lumpectomy shell, compression can be applied to ensure that the silicone gel conforms to the natural surrounding tissue such that upon cross-linking and curing, the silicone gel filled implant blends with the natural breast tissue, whereby no defects are visible.

Physical Defect. As used herein, the term "physical defect" refers to any flaw or imperfection present in an implanted medical device. Such physical defects can include gel fracture (e.g., cracks in the gel), one or more lumps, wrinkling, and/or demarcation. The presently described RCS compositions can be used to ameliorate or eliminate any such physical defect present in an existing implanted medical device. After injection and gelling and/or cure of the present RCS composition, a body implant is free from any physical defects, and/or any existing physical defect is ameliorated or eliminated. The implanted medical device can be a silicone gel containing implant.

Pot Life. As used herein, the term "pot life" refers to the period of time that the presently described RCS composition, after mixing, remains low enough in viscosity that it can still be sufficiently flowable such that it can be injected into an implanted device, e.g., via an 18 to 21 gauge needle. The terms "pot life" and "working life" as used interchangeably herein.

Silicone Gel. As used herein, the term "silicone gel" refers to any cross-linked, gelled, or cured, silicone gel formulation or composition.

Mixer. As used herein, the term "mixer" refers to a mechanical mixer configured to mix two components of the presently described two-component system and kit, prior to injection. Such mixers can include static mixers, including known static mixers, e.g., produced by PVA, Cohoes, N.Y.

Two components, namely the catalyst fluid and the cross-linker fluid, can also be mixed by combining these fluids in a container, and then mixing by any known means, such as by mechanical stirring or shaking, until substantially mixed, prior to injecting. Alternatively two components namely the catalyst fluid and the cross-linker fluid can be mixed by placing these fluids into two separate syringes and connecting these syringes by a connector and then transferring the fluids from one syringe to another back and forth several times, until substantially mixed, prior to injecting.

Subject. As used herein, the term "subject" refers to any animal including for example, a human, having a flexible implanted medical device.

Tissue Expander. As used herein, the term "tissue expander" refers to an inflatable implant designed to stretch the skin and muscle. Tissue expanders can be permanent or non-permanent tissue expanders. Suitable breast tissue expanders can include but are not limited to breast tissue expanders including MENTOR® tissue expanders, e.g., CPX®3, CPX®4, ARTOURA™; and ALLERGAN Tissue Expanders. Tissue expanders can also include other tissue expanders, for example, calf tissue expanders.

Injection Device. As used herein, the term "injection device" refers to a device configured to administer by injection, an RCS composition comprising two reactive components that cannot be supplied or stored as a single mixture. Such devices can include dual prefilled syringes each containing a respective component, connected via, e.g., a Y-connector optionally comprising a mixer, e.g., a static mixer; and dual cartridge dispensing systems, including for example, those produced by PLAS-PAK Industries, Inc., Norwich, Conn., which can be used with static mixers and include syringes having variable volumes up to 750 ml per cartridge, and include cartridge combinations that produce various mix ratios. Other suitable devices can include, but are not limited to, dual bore devices, and dual chamber syringes. Dual chamber syringes can include, for example, those manufactured by Credence MedSystems, Inc., Menlo Park, Calif., which include Companion Dual Chamber Syringe liquid-liquid.

According to the presently described subject matter, an injection device can comprise a syringe with attached hypodermic needle, where the syringe is filled with the already mixed RCS composition.

Rapidly Cross-Linkable Silicone Compositions and Methods

The presently described subject matter is directed to novel, injectable, RCS compositions for filling an implanted medical device in situ, where the compositions can be injected as a pre-mixed formulation, or can be injected as a two-part formulation, via, for example, a injection device configured to separate the two components, where the components mix upon administration, e.g., injection into an implanted medical device. The presently described RCS formulations are injectable via a hypodermic syringe comprising e.g., an 18 to 21 gauge needle.

The presently described RCS two-part formulation (where mixing and injecting are performed substantially simultaneously through an injection device that separates the components up to point of use), as well as the pre-mixed formulation (where the components are first mixed and then injected, e.g., through a single syringe), contain no solvent or substantially no solvent that would need to be removed during or after curing.

Upon mixing, either prior to injection (pre-mixed formulation) or substantially simultaneous with injection (two-component formulation), the components of the presently described formulations react and within minutes form a gel inside the implanted medical device. Upon mixing or mixing and substantially simultaneous injection, the RCS composition has a pot life of about ≤five min., where the mixture maintains low viscosity and high flowability, such that it can be injected using a hypodermic needle, e.g., an 18 to 21 gauge hypodermic needle, where the RCS composition substantially gels, and cures, in situ in the implanted medical device.

The presently described injectable, two-part RCS formulations can comprise or consist of two highly flowable low viscosity fluids, which rapidly cross-link upon mixing and injection, such that the RCS composition gels and fully cures in-situ, at ambient or body temperature inside an implanted medical device. When, prior to injection, the implanted medical device comprises a conventional silicone gel, the presently described RCS gel can have substantially the same properties as that of the conventional silicone gel.

Each component of a RCS two-component formulation can be provided in a respective first and second syringe of an injection device, the syringes connected via a Y-connector connected to a mixer, e.g., a static mixer. Alternatively, the present RCS compositions can also be pre-mixed and then injected via a single syringe.

In some embodiments, the size of an implanted medical device containing conventional thermally cured silicone gel, can be increased, as needed, by infusing, e.g., by injecting, the presently described RCS composition into the implanted medical device, where the present composition then rapidly gels and cures in situ. The gel contained in the resulting enlarged implant including the RCS gel and the conventional silicone gel, is homogeneous and consistent throughout with regard to its physical properties and can be free from physical defect, e.g., no lumps or gel fracture observed in the implanted medical device.

In other aspects, saline contained in implanted non-permanent tissue expanders can be replaced with the present RCS composition. In other aspects, the saline in saline filled breast implants can be replaced with the presently described RCS compositions.

The RCS composition can have a viscosity at ≤5 min. post-mixing, that is sufficiently low so that the composition is flowable and can be injected via an 18 to 21 gauge needle. Suitable viscosities can include ≤300 cPs, ≤250 cPs, ≤200 cPs, ≤150 cPs, ≤100 cPs, from about 80 cPs to about 300 cPs, from about 100 cPs to about 300 cPs, from about 100 cPs to about 250 cPs, from about 200 cPs to about 300 cPs, from about 100 cPs to about 250 cPs, from about ≥80 cPs to about ≤300 cPs, from about ≥100 cPs to about ≤300 cPs, from about ≥125 cPs to about ≤300 cPs, or from about ≥150 cPs to about ≤275 cPs. The viscosity ≤5 min. post-mixing, can be ≤250 cPs.

The presently described RCS composition according to the presently described subject matter can gel, post-mixing, in an amount of time from about ≥5 min., >5 min., or from about 5 min. to about 15 min. The presently described RCS compositions can gel in about ≥5 min., or from about 6 to 10 min., and can form a fully cured gel within about 12 hours or within about 24 hours.

The presently described RCS composition according to the presently described subject matter can cure in ≤12 hrs., ≤24 hrs., from about 6 hrs. to about 24 hrs. from about 6 hrs. to about 12 hrs., about 8 hrs., about 10 hrs., about 12 hrs., about 14 hrs., about 18 hrs., about 22 hrs., or about 24 hrs.

The viscosity of the presently described RCS compositions increases post-injection such that the gel cannot flow; thus any leakage of the gel from the implant through the injection hole is not possible. The formed gel plugs any channels left by an infusion needle in the implant. The RCS compositions can be injected through a wall of an implant shell, and do not have to be injected via a valve or a port. Further, injection can be through a double-walled or double-walled area of a shell of an implant. A double-walled shell or shell area also can serve to prevent any potential leakage. When injection of the present RCS composition is into an implanted device containing conventional silicone, the RCS composition can be injected behind a portion of the conventional silicone, which can prevent any potential leakage.

The presently described RCS composition, injectable, for example, as a two-part formulation, can include a first container comprising a catalyst fluid comprising a platinum divinyl disiloxane complex and a low viscosity vinyl terminated polydimethylsiloxane; and a second container comprising a cross-linker fluid comprising a low viscosity vinyl terminated polydialkylsiloxane, a low viscosity hydride terminated polydimethylsiloxane, and a silicone cross-linker. Suitable cross-linkers include but are not limited to polymethylhydrosiloxane polydimethylsiloxane copolymer.

The presently described an injectable, RCS composition, can comprise or consist of a catalyst fluid comprising a first low viscosity vinyl terminated polydimethylsiloxane present in an amount of from about 97 wt % to about 99.5 wt % based on the weight of the catalyst fluid and having a viscosity of from about 1 to about 150 cPs, and a platinum divinyl disiloxane complex having from about 2 to about 32 ppm Pt based on the catalyst fluid, wherein the catalyst fluid has a viscosity of from about 1 to about 150 cPs; and a cross-linker fluid comprising a second low viscosity vinyl terminated polydimethylsiloxane present in an amount of from about 1 wt % to about 40 wt % based on the weight of the cross-linker fluid and having a viscosity of from about 1 to about 150 cPs, a low viscosity hydride terminated polydimethylsiloxane present in an amount of from about 60 wt % to about 90 wt % based on the weight of the cross-linker fluid and having a viscosity of from about 1 to about 150 cPs, and a siloxane cross-linker present in an amount of from about 0.32 wt % to about 5.0 wt % based on the weight of the cross-linker fluid, and having a viscosity of from about 1 to about 150 cPs. wherein the cross-linker fluid has a viscosity of from about 1 to about 150 cPs, and wherein post-preparation, the resultant RCS composition has a viscosity of ≤150 cPs for at least one minute and a pot-life of ≤5 min., at ambient temperature. The resultant RCS composition can have a Pt content of from about 1 ppm to about 16 ppm. The catalyst fluid can be provided in a first container and the cross-linker fluid can be provided in a second container.

Such implanted medical devices can include, but are not limited to: breast implants including for example, any known breast implant, an adjustable implant, for example, a multi-lumen breast implant, where the implant can comprise an inner and an outer envelope, the breast implant can comprise one or more valves and/or ports, optionally including flexible tubing; lumpectomy implants; calf implants; tissue expanders, including but not limited to, breast tissue expanders, and calf tissue expanders; and any other gel or fluid filled body implant useful for cosmetic and/or reconstructive purposes. Suitable tissue expanders can include permanent tissue expanders.

Implanted medical devices can include, but are not limited to those medical implant devices according to the presently described subject matter. An implant shell can comprise a single-walled shell or a double-walled shell and/or one or more areas that are one or more of a single-walled area and a double-walled area.

The present low viscosity vinyl terminated siloxane polymers can include vinyl terminated polydialkylsiloxane, including vinyl terminated polydimethylsiloxane, including DMS-V21 and DMS-V22 available from GELEST, Morrisville, Pa. Vinyl terminated polydimethylsiloxane, DMS-V21 can be used in the presently described RCS compositions.

Suitable low viscosity hydride terminated polydimethylsiloxanes can include, but are not limited to, DMS-H21 available from GELEST, Morrisville, Pa. Suitable siloxane cross-linkers for use in the presently described compositions can include methylhydride siloxane dimethyl siloxane copolymer, available from GELSET HMS-301, and HMS-501, Morrisville, Pa.

Other cross-linkers can include, for example, silicone cross-linking agents including, for example, polymethylhydrosiloxane, polymethylhydro-co-polydimethylsiloxane, polyethyhydrosiloxane, polymethylhydrosiloxane-co-octylmethylsiloxane, and polymethylhydrosiloxane-co-methylphenylsiloxane.

Suitable platinum divinyl disiloxane complex catalyst, can include Karstedt catalyst, e.g., $Pt[(CH_2=CH)(CH_3)_2SiOSi(CH_3)_2(CH=CH_2)]_3$, including Gelest SIP 6831.2 available from GELEST, Morrisville, Pa. Suitable catalysts are described in U.S. Pat. No. 3,775,452, incorporated herein by reference in its entirety.

The presently described catalyst fluid component can comprise platinum divinyl disiloxane having a platinum content of from about 2 ppm to about 32 ppm, from about 4 ppm to about 28 ppm, from about 4 ppm to about 20 ppm, from about 6 ppm to about 14 ppm, from about 6 ppm to about 12 ppm, from about 4 ppm to about 12 ppm, from about 4 ppm to about 6 ppm, from about 4 ppm to about 8 ppm, about 4 ppm, about 6 ppm, about 8 ppm, about 10 ppm, about 12 ppm, about 14 ppm, about 20 ppm, about 26 ppm, or about 32 ppm.

The platinum content of the presently described RCS composition can be from about 1 ppm to about 16 ppm, from about 1 ppm to about 10 ppm, from about 1 ppm to about 8 ppm, from about 2 ppm to about 10 ppm, from about 2 ppm to about 8 ppm, from about 1 ppm to about 6 ppm, from about 1 ppm to about 4 ppm, about 2 ppm, about 3 ppm, about 4 ppm, about 5 ppm, about 6 ppm, about 7 ppm, or about 8 ppm.

The presently described platinum divinyl disiloxane can have a viscosity of from about 1 to about 150 cPs or from about 80 to 120 cPs. The presently described catalyst fluid can have a viscosity of from about 1 to about 150 cPs or from about 80 to 120 cPs.

The presently described first low viscosity vinyl terminated polydimethylsiloxane can be present in the catalyst fluid in an amount of from about 96 wt % to about 99.5 wt %, of from about 96.5 wt % to about 99.5 wt %, of from about 97 wt % to about 99.5 wt %, of from about 97.25 wt % to about 99.25 wt %, of from about 97.5 wt % to about 99 wt %, of from about 97.75 wt % to about 98.75 wt %, of from about 98 wt % to about 98.5 wt %, of from about 98 wt % to about 98.25 wt %, of from about 97.5 wt % to about 98.5 wt %, of from about 97.75 wt % to about 98.75 wt %, about 97 wt %, about 97.5 wt %, about 98 wt %, about 98.4 wt %, about 98.5 wt %, about 99 wt %, or about 99.5 wt %.

The presently described first low viscosity vinyl terminated polydimethylsiloxane and the second low viscosity vinyl terminated polydimethylsiloxane, together, can be present in the RCS composition in an amount of from about 45 wt % to about 95 wt %, from about 50 wt % to about 90 wt %, from about 55 wt % to about 85 wt %, from about 60 wt % to about 80 wt %, from about 65 wt % to about 75 wt %, about 60 wt %, about 65 wt %, about 70 wt %, about 75 wt %, about 80 wt %, about 85 wt %, or about 90 wt %.

The presently described first low viscosity vinyl terminated polydimethylsiloxane can have a viscosity of from about 1 to about 150 cPs or from about 80 to 120 cPs.

The presently described second low viscosity vinyl terminated polydimethylsiloxane can be present in the cross-linker fluid in an amount of from about 1 wt % to about 40 wt %, of from about 5 wt % to about 40 wt %, of from about 5 wt % to about 35 wt %, of from about 7 wt % to about 32 wt %, of from about 8 wt % to about 31 wt %, of from about 10 wt % to about 30 wt %, of from about 12 wt % to about 38 wt %, of from about 14 wt % to about 26 wt %, of from about 15 wt % to about 25 wt %, of from about 18 wt % to about 23 wt %, from about 19 wt % to about 22 wt %, from about 17 wt % to about 22 wt %, from about 18 wt % to about 21 wt %, from about 19 wt % to about 20 wt %, about 15 wt %, about 16 wt %, about 17 wt %, about 18 wt %, about 19 wt %, about 19.5 wt %, about 20 wt %, about 21 wt %, or about 22 wt %.

The presently described second low viscosity vinyl terminated polydimethylsiloxane can have a viscosity of from about 1 to about 150 cPs or from about 80 to 120 cPs. The presently described cross-linker fluid can have a viscosity of from about 1 to about 150 cPs or from about 80 to 120 cPs.

The presently described low viscosity hydride terminated polydimethylsiloxane is present in the cross-linker composition in an amount of from about 55 wt % to about 95 wt %, of from about 60 wt % to about 90 wt %, of from about 65 wt % to about 85 wt %, of from about 70 wt % to about 85 wt %, of from about 75 wt % to about 85 wt %, of from about 76 wt % to about 84 wt %, of from about 77 wt % to about 83 wt %, of from about 78 wt % to about 82 wt %, of from about 79 wt % to about 81 wt %, about 77 wt %, about 78 wt %, about 79 wt %, about 80 wt %, about 80.5 wt %, about 81 wt %, about 82 wt %, about 83 wt %, or about 84 wt %.

The presently described low viscosity hydride terminated polydimethylsiloxane can be present in the RCS composition in an amount of from about 25 wt % to about 55 wt %, from about 30 wt % to about 50 wt %, from about 35 wt % to about 45 wt %, about 30 wt %, about 35 wt %, about 40 wt %, about 45 wt %, or about 50 wt %.

The presently described low viscosity hydride terminated polydimethylsiloxane can have a viscosity of from about 1 to about 150 cPs or from about 80 to 120 cPs.

The presently described siloxane cross-linker is present in the cross-linker fluid component in an amount of from about 0.1 wt % to about 7 wt %, from about 0.15 wt % to about 6 wt %, from about 0.2 wt % to about 6 wt %, from about 0.3 wt % to about 6 wt %, from about 0.32 wt % to about 5 wt %, from about 0.4 wt % to about 4 wt %, from about 0.4 wt % to about 3 wt %, from about 0.3 wt % to about 2 wt %, from about 0.3 wt % to about 3 wt %, from about 0.3 wt % to about 1 wt %, from about 0.4 wt % to about 3 wt %, from about 0.4 wt % to about 2 wt %, from about 0.6 wt % to about 3 wt %, from about 0.7 wt % to about 2 wt %, from about 0.8 wt % to about 2 wt %, from about 1 wt % to about 2 wt %, from about 1.2 wt % to about 1.8 wt %, from about 0.2 wt %, about 0.3 wt %, about 0.32 wt %, about 0.4 wt %, about 0.5 wt %, about 0.6 wt %, about 1 wt %, about 1.4 wt %, about 1.6 wt %, about 1.8 wt %, about 2 wt %, about 2.5 wt %, about 3 wt %, about 3.5 wt %, about 4 wt %, about 4.5 wt %, or about 5 wt %.

The presently described siloxane cross-linker can be present in the RCS composition in an amount of from about 0.05 wt % to about 3.5 wt % of from about 0.1 wt % to about 3 wt %, of from about 0.16 wt % to about 2.5 wt %, of from about 0.2 wt % to about 2.5 wt %, of from about 0.2 wt % to about 2 wt %, of from about 0.25 wt % to about 2 wt %, of from about 0.3 wt % to about 2 wt %, of from about 0.13 wt % to about 2.2 wt %, of from about 0.14 wt % to about 2.1 wt %, of from about 0.15 wt % to about 2.1 wt %, of from about 0.16 wt % to about 2 wt %, from about 0.18 wt % to about 1.8 wt %, from about 0.2 wt % to about 1.6 wt %, from about 0.4 wt % to about 1.4 wt %, from about 0.6 wt % to about 1.2 wt %, from about 0.8 wt % to about 1 wt %, about 0.15 wt %, about 0.2 wt %, about 0.3 wt %, about 0.4 wt %, about 0.5 wt %, about 0.6 wt %, about 0.8 wt %, about 1 wt %, about 1.2 wt %, about 1.4 wt %, about 1.6 wt %, about 1.8 wt %, about 2 wt % or about 2.5 wt %.

The presently described siloxane cross-linker can have a viscosity of from about 1 to about 150 cPs or from about 25 to 35 cPs.

The presently described two-part formulation of the present RCS composition is flowable and has a viscosity <150 cPs for at least 1 minute after forming or mixing at ambient temperature. The composition has a viscosity >300 cPs at about 10 minutes after forming or mixing at ambient temperature. The gelled composition can have a viscosity ≥50,000 cPs≤24 after forming or mixing and/or injecting at ambient temperature.

The presently described RCS pre-mixed formulation, injectable, for example, after mixing via a single syringe, can include the platinum divinyl disiloxane complex having a Pt content of from about 1 ppm to about 16 ppm as described herein, the low viscosity vinyl terminated polydimethylsiloxane can be present in an amount of from about 55.0 wt % to about 80.0 wt %, the low viscosity hydride terminated polydimethylsiloxane can be present in an amount of from about 35.0 wt % to about 45.0 wt %, and the cross-linker can be present in an amount of from about 0.16 wt % to about 2.5 wt %. The presently described RCS composition can include the low viscosity vinyl terminated polydimethylsiloxanes present in an amount of about 60 wt %, the low viscosity hydride terminated polydimethylsiloxanes present in an amount of about 40 wt %, and the siloxane cross-linker is present in an amount of about 0.16 wt %.

The presently described two-part formulations of the presently described RCS compositions can be prepared for injection into an implanted medical device, the method can comprise a method for adjusting the volume of an implanted medical device; ameliorating or eliminating a physical defect in a filled implanted medical device, including for example, lumps, wrinkles, gel fractures, demarcation, or any other physical defect; filling or gradually filling an implanted, unfilled tissue expander; replacing saline in an implanted medical device comprising saline; filling an unfilled envelope or shell of an implanted device, including for example an adjustable breast implant; or employing the present composition in a permanent tissue expander in place of saline.

The methods as described herein, including for example, filling, adjusting, replacing, expanding, and ameliorating, can comprise the following steps: providing the rapidly cross-linkable silicone composition or kit according to the presently described subject matter; mixing the catalyst fluid with the cross-linker fluid to produce an injectable composition having an initial viscosity of <150 cPs for at least about 1 min.; and within ≤5 min. of initiating mixing, and substantially simultaneous with mixing, or immediately after mixing, for example, within 5 minutes of mixing, injecting a predetermined volume of the injectable composition into the implanted medical device in situ, whereby the rapidly cross-linkable silicone composition substantially cross-links and gels in situ in an amount of time ≥5 min. to produce a filled implant comprising a homogeneous rapidly cross-linkable silicone gel, wherein the rapidly cross-linkable silicone gel has a viscosity as described herein, for example, ≥50,000 cPs, or ≥200,000 cPs≥60 min. post-injection at ambient temperature. The presently described rapidly cross-linkable silicone gel can have a ≥50,000 cPs≤24 post-injection at ambient temperature.

The injected RCS gel remains in the implant post-injection without leakage of the gel from the injection site.

The presently described RCS filled implant can be free from any physical defect. When the present method is directed to eliminating or ameliorating a physical defect present in an implanted medical device, the physical defect is ameliorated or eliminated post-injection (or post-injection and post-gelling and/or post-cure) of the present RCS composition.

Any one or more of the methods as described herein, can comprise: mixing, for example, rapidly mixing, for example at an ambient temperature, a catalyst fluid and a cross-linker fluid of the presently described two-component formulation of the present RCS composition, the produced RCS composition having an initial viscosity of <150 cPs; within about 5 minutes post-mixing, injecting produced RCS composition into the implanted medical device, for example, an implanted medical device as described herein, through a hypodermic needle of an injection device, e.g., using for example, one or more syringes, according to the presently described subject matter; allowing the injected RCS composition to cross-link, for example, for a period of time sufficient for the injected composition to gel, inside the implant at an ambient temperature; and withdrawing the hypodermic needle from the implant, whereby the injected RCS gel remains in the implant post-injection without leakage of the gel from the injection site. The injection device can comprise an injection device as presently described herein including a hypodermic needle that is an 18 to 21 gauge needle.

Any one or more steps of the presently described method may or may not be carried out at ambient temperature. Ambient temperature is from about 18° C. to about 40° C., as described herein.

According to the presently described subject matter, at least the steps of injecting and allowing are carried out at ambient temperature, including, e.g., room temperature. The step of allowing can be carried out at normal body temperature.

The steps of mixing and injecting can be carried out simultaneously, substantially simultaneously, or sequentially.

The step of withdrawing can comprise withdrawing the needle immediately post-injection, from about 0.02 to 5 min. post-injection, from about 0.05 to about 1 min., from about 0.05 to about 2 min., from about 0.05 to about 3 min., from about 0.1 to about 3 min. from about 0.2 to about 3 min., from about 0.2 to about 2 min., from about 0.2 to about 1 min., from about 0.2 to about 0.5 min., from about 0.3 to about 3 min., from about 0.3 to about 1 min., about 0.05 min., about 0.1 min., about 0.2 min., about 0.3 min., about 0.4 min., about 0.5 min., or about 1 min.

An injection scheme can include injecting the presently described pre-mixed RCS formulation of the present RCS composition through a single syringe including injection needle, e.g., an 18-21 gauge needle, into a silicone filled implanted medical device, according to the presently described subject matter.

Another injection scheme can include injecting the presently described two-part RCS formulation, including a catalyst fluid and a cross-linker fluid, into an implanted medical device, e.g., a silicone breast implant through an injection device including two syringes and a mixing tip, where one syringe comprises the catalyst fluid and the other syringe comprises the cross-linker fluid. Upon actuating the pair of plungers of the syringes of the injection device, the two fluids intimately mix in the mixing tip, to form a homogeneous mass which rapidly cross-links post-mixing and post-injection, where the two-part formulation is simultaneously mixed in the mixing tip and injected into the implanted device, e.g., an implanted breast implant.

EXAMPLES

Example 1: Preparation and of Pre-Mixed Formulation of a Rapidly Cross-Linkable Silicone Composition with Variable Platinum Content In this Example, the RCS compositions were pre-mixed prior to injection, i.e., were injected as a single composition. The resulting mixtures remained injectable with low viscosity up to 5 minutes post-mixing, and were easily flowable through a hypodermic needle after mixing. The process window (pot-life) was about 5 minutes prior to injection. The preparation of the composition was as follows:

Step 1. Catalyst Fluid Preparation:

1 g of Karstedt catalyst Platinum divinyl disiloxane complex, containing 2% $Pt[(CH_2=CH)(CH_3)_2SiOSi(CH_3)_2(CH=CH_2)]_3$ in xylene (obtained from GELSET SIP 6831.2) was mixed with 99 g of low viscosity (100 cPs)

vinyl terminated polydimethylsiloxane (GELSET DMS V21) for 5 minutes at ambient temperature to obtain a homogeneous solution.

Step 2. Cross-Linker Fluid Preparation:

For each of the test compositions 1-4 set forth in Table 1 below, 60 g of low viscosity vinyl terminated polydimethylsiloxane (Gelest DMS V21) was mixed with 40 g of low viscosity hydride terminated polydimethylsiloxane (GELEST DMS H21), and 0.16 g cross linker (methylhydride siloxane dimethyl siloxane copolymer, GELEST HMS301).

Step 3. Rapidly Cross-Linkable Silicone Composition Preparation:

0.5 g, 1.0 g, 2.0 g, and 3.0 g of the catalyst fluid of step 1, was added to a respective cross-linker fluid composition of Step 2, and stirred vigorously for 1 minute, to produce test compositions 1-4, each having a different platinum content, respectively, as set forth in Table 1 below.

TABLE 1

Catalyst content of four one-part RCS compositions

| Test Composition | Test composition Pt content | Amount of catalysts solution added (g) |
|---|---|---|
| 1 | 1 ppm | 0.5 |
| 2 | 2 ppm | 1.0 |
| 3 | 4 ppm | 2.0 |
| 4 | 6 ppm | 3.0 |

The viscosity of the resulting formulations was measured by a Brookfield viscometer over a period of 30 minutes. Measurements were performed every minute and the results are summarized in Table 2, below.

TABLE 2

Viscosity (cPs) of RCS compositions having different Pt content over time

| Time (min) | Viscosity RCS composition 1 (cPs) | Viscosity RCS composition 2 (cPs) | Viscosity RCS composition 3 (cPs) | Viscosity RCS composition 4 (cPs) |
|---|---|---|---|---|
| 2 | 100 | 100 | 110 | 120 |
| 3 | 100 | 107 | 140 | 165 |
| 4 | 100 | 123 | 190 | 235 |
| 5 | 100 | 142 | 260 | 325 |
| 6 | 105 | 166 | 340 | 435 |
| 7 | 115 | 196 | 440 | 560 |
| 8 | 120 | 227 | 545 | 690 |
| 9 | 135 | 257 | 660 | 820 |
| 10 | 145 | 296 | 780 | 950 |
| 11 | 150 | 338 | 905 | 1075 |
| 12 | 160 | 383 | 1010 | |
| 13 | 175 | 435 | | |
| 14 | 190 | 483 | | |
| 15 | 200 | 535 | | |
| 16 | 215 | 580 | | |
| 17 | 230 | 630 | | |
| 18 | 245 | 690 | | |
| 19 | 260 | 750 | | |
| 20 | 280 | 800 | | |
| 21 | 290 | 860 | | |
| 22 | 310 | 930 | | |
| 23 | 330 | 970 | | |
| 24 | 345 | 1025 | | |
| 25 | 365 | | | |
| 26 | 375 | | | |
| 27 | 395 | | | |
| 28 | 415 | | | |
| 29 | 435 | | | |
| 30 | 455 | | | |

The curing of the RCS test compositions is shown by monitoring viscosity of the mixtures. Higher Pt content resulted in a faster increase of viscosity. All mixtures completely stopped flowing after 2 hours.

Example 2: Preparation and of Pre-Mixed Formulation of a Rapidly Cross-Linkable Silicone Composition with Variable Cross-Linker Content The formulation of this Example includes a cross-linker content 10 times that of Example 1. The mixtures of this example also remained low viscosity up to 5 minutes post-mixing, and were easily flowable through a hypodermic needle after mixing, despite the increased cross-linker content as compared to Example 1. The preparation of the composition was as follows:

Step 1. Catalyst Fluid Preparation:

1 g of Karstedt catalyst (Platinum divinyl disiloxane complex, GELEST SIP 6831.2) containing 2% $Pt[(CH_2\!=\!CH)(CH_3)_2SiOSi(CH_3)_2(CH\!=\!CH_2)]_3$ in xylene, was mixed with 99 g of low viscosity (100 cPs) vinyl terminated polydimethylsiloxane (GELEST DMS V21) for 5 minutes at ambient temperature to obtain a homogeneous solution.

Step 2. Cross-Linker Fluid Preparation:

For each of test compositions 5-7 set forth in Table 3 below, 60 g of low viscosity vinyl terminated polydimethylsiloxane (GELEST DMS V21) was mixed with 40 g of low viscosity hydride terminated polydimethylsiloxane (GELEST DMS H21), and 1.6 g cross linker (methylhydride siloxane dimethyl siloxane copolymer, GELEST HMS301).

Step 3. Rapidly Cross-Linkable Silicone Composition Preparation 0.5, 1.0, and 3.0 g of the catalyst fluid of step 1, was added to a respective cross-linker fluid composition of step 2, and stirred vigorously for 1 minute, to produce the present injectable test compositions 5-7, respectively, as set forth in Table 3 below.

TABLE 3

Catalyst content of three one-part RCS compositions

| Test Composition | Test composition Pt content | Amount of catalysts solution added (g) |
|---|---|---|
| 5 | 1 ppm | 0.5 |
| 6 | 2 ppm | 1.0 |
| 7 | 6 ppm | 3.0 |

The viscosity of the resulting test compositions was measured by a Brookfield viscometer over a period of 30 minutes. Measurements were performed every minute and the results are summarized in Table 4, below.

TABLE 4

Viscosity (cPs) of RCS compositions having different Pt content over time

| Time (min) | Viscosity RCS composition 5 (cPs) | Viscosity RCS composition 6 (cPs) | Viscosity RCS composition 7 (cPs) |
|---|---|---|---|
| 2 | 100 | 100 | 100 |
| 3 | 100 | 105 | 140 |
| 4 | 100 | 115 | 174 |
| 5 | 105 | 124 | 213 |
| 6 | 105 | 134 | 269 |
| 7 | 115 | 144 | 351 |
| 8 | 115 | 155 | 524 |
| 9 | 120 | 168 | 865 |

TABLE 4-continued

Viscosity (cPs) of RCS compositions having different Pt content over time

| Time (min) | Viscosity RCS composition 5 (cPs) | Viscosity RCS composition 6 (cPs) | Viscosity RCS composition 7 (cPs) |
| --- | --- | --- | --- |
| 10 | 125 | 183 | 1487 |
| 11 | 130 | 198 | |
| 12 | 140 | 216 | |
| 13 | 145 | 237 | |
| 14 | 150 | 258 | |
| 15 | 160 | 285 | |
| 16 | 165 | 315 | |
| 17 | 175 | 350 | |
| 18 | 180 | 402 | |
| 19 | 190 | 435 | |
| 20 | 200 | 537 | |
| 21 | 210 | 635 | |
| 22 | 220 | 910 | |
| 23 | 230 | 1168 | |
| 24 | 240 | | |
| 25 | 255 | | |
| 26 | 280 | | |
| 27 | 320 | | |
| 28 | 325 | | |
| 29 | 330 | | |
| 30 | 350 | | |

The curing of the present RCS compositions is shown by monitoring viscosity of the mixtures. Higher Pt content resulted in faster increase of viscosity. All mixtures completely stopped flowing after 1 hour.

The viscosities of the fully cured systems were over 50,000 cPs and beyond the measurement limit of the equipment.

Example 3: Injection of Rapidly Cross-Linkable Silicone Composition into Implant A standard cured silicone gel filled implant (MENTOR, Johnson & Johnson, N.J.) was injected with the inventive composition of Example 1, containing 4 ppm Pt, immediately after mixing the composition using a syringe with an 18 gauge needle and forming a bolus of RCS composition inside the already cross-linked gel of the implant.

It was observed that the bolus formed a homogenous invisible and cured silicone mass inside the implant. No leakage of injected silicone composition was observed. Full curing of the injected silicone composition was observed within less than 24 hours at ambient temperature.

Example 4: Preparation and of Two-Part Formulations of a Rapidly Cross-Linkable Silicone Composition A catalyst component fluid and a cross-linkable silicone component fluid were prepared and stored separately. The two components were injected as a two-part system through a mixing Y-connector with static mixers directly into conventional gel implants. The dual syringe used was equipped with a direct thread static mixer and manufactured by Plas-Pak Industries, Inc, Norwich, Conn.

The catalyst component fluid was prepared by mixing 37.7 g of low viscosity vinyl terminated polydimethylsiloxane (GELEST DMS V21) with 0.6 g of catalyst (described in Example 1, above, i.e., 2% catalyst in xylene) for 5 minutes.

The cross-linkable silicone component fluid was prepared by mixing 7.3 g of low viscosity vinyl terminated polydimethylsiloxane (GELEST DMS V21) with 30 g of low viscosity hydride terminated polydimethylsiloxane (GELEST DMS H21), (methylhydride siloxane dimethyl siloxane copolymer, GELEST HMS301) for 5 minutes.

The catalyst component and the cross-linkable silicone component fluids, each contained in a separate syringe, were injected together through a mixing Y-connector equipped with a static mixer terminating with a 18 gauge hypodermic needle. The injection was directly into the silicone gel filled implant. The resulting enlarged breast implant appears homogeneous and consistent throughout on its physical properties. No lumps observed in the injectable portion of the implant.

Example 5: Testing RCS Formulations of Various Viscosities for Injecting Through Hypodermic Needles of Different Gauges RCS formulations 8-11 having various standard viscosities were analyzed and injectability through needles of several sizes was assessed.

The silicone viscosity standard fluids were purchased from Brookfield Engineering Laboratories Inc, Middleboro Mass.

TABLE 5

Assessment of injections through various gauge needles of silicone viscosity standard fluids having different viscosities

| Test Composition | Viscosity of standard fluid | Needle gauge 15 (largest) | Needle gauge 18 (intermediate) | Needle gauge 21 (smallest) |
| --- | --- | --- | --- | --- |
| 8 | Viscosity 100 cPs | Composition passes through by hand operated syringe | Composition passes through by hand operated syringe | Composition passes through by hand operated syringe |
| 9 | Viscosity 200 cPs | Composition passes through by hand operated syringe | Composition passes through by hand operated syringe | Composition passes through by hand operated syringe |
| 10 | Viscosity 300 cPs | Composition passes through by hand operated syringe | Composition passes through by hand operated syringe | Some difficulty in passing composition through by hand operated syringe |
| 11 | Viscosity 500 cPs | Composition passes through by hand operated syringe | Some difficulty in passing composition through by hand operated syringe | Composition does not pass through by hand operated syringe |

This Example illustrates that all of the present RCS formulations shown in Examples 1-2 are injectable, even through the smallest, i.e., 21 gauge needles, with workable shelf life of 5 minutes, having viscosities less than or about equal to ~300 cPs.

The following claims particularly point out certain combinations and subcombinations that are directed to an aspect of the presently described subject matter and are novel and non-obvious. Subject matter embodied in other combinations and subcombinations of features, functions, elements and/or properties may be claimed through amendment of the present claims or presentation of new claims in this or a related application.

The invention claimed is:

1. A method of filling an implanted medical device in situ, comprising:
   providing a two-part rapidly cross-linkable silicone composition, comprising:
      a catalyst fluid comprising
         a first low viscosity vinyl terminated polydimethylsiloxane present in an amount of from about 97 wt % to about 99.5 wt % based on the weight of the catalyst fluid and having a viscosity of from about 1 to about 150 cPs, and
         a platinum divinyl disiloxane complex comprising Pt[(CH2=CH)(CH3)2SiOSi(CH3)2(CH=CH2)]3 having a platinum content of from about 2 ppm to about 32 ppm based on the catalyst fluid,
      wherein the catalyst fluid has a viscosity of from about 1 to about 150; and
      a cross-linker fluid comprising
         a second low viscosity vinyl terminated polydimethylsiloxane present in an amount of from about 1 wt % to about 40 wt % based on the weight of the cross-linker fluid and having a viscosity of from about 1 to about 150 cPs,
         a low viscosity hydride terminated polydimethylsiloxane present in an amount of from about 60 wt % to about 90 wt % based on the weight of the cross-linker fluid and having a viscosity of from about 1 to about 150 cPs, and
         a silicone cross-linker comprising polymethylhydrosiloxane polydimethylsiloxane copolymer present in an amount of from about 0.32 wt % to about 5.0 wt % based on the weight of the cross-linker fluid, and having a viscosity of from about 1 to about 150 cPs,
      wherein the cross-linker fluid has a viscosity of from about 1 to about 150 cPs, and
      wherein post-preparation or post-mixing of the catalyst fluid and the cross-linker fluid, the resultant rapidly cross-linkable silicone composition has a viscosity of ≤150 cPs for ≥1 min. post-preparation and ≤300 cPs≤5 min. post-preparation, at ambient temperature, and the resultant rapidly cross-linkable silicone composition has a platinum content of from about 1 ppm to about 16 ppm;
   mixing the catalyst fluid with the cross-linker fluid to produce an injectable composition having an initial viscosity of <150 cPs for at least about 1 min.; and
   within ≤5 min. of initiating mixing, injecting a predetermined volume of the injectable composition into the implanted medical device in situ, whereby the rapidly cross-linkable silicone composition substantially cross-links and gels in situ in an amount of time ≥5 min. to produce a filled implant comprising a homogeneous rapidly cross-linkable silicone gel,
   wherein the rapidly cross-linkable silicone gel has a viscosity ≥50,000 cPs≤24 hrs. post-injection at ambient temperature.

2. The method of claim 1, wherein the implanted medical device comprises silicone.

3. The method of claim 1, wherein the filled implant is free from any physical defect.

4. The method of claim 1, wherein post-injection, there is no leakage of the silicone gel from the filled implant at the injection site.

5. The method of claim 1, wherein the implanted medical device comprises a breast implant, an adjustable breast implant, a calf implant, a tissue expander, or a lumpectomy implant.

6. The method of claim 5, wherein the implanted medical device comprises:
   at least one empty envelope, and injecting comprises injecting into the empty envelope; and/or
   at least one silicone containing envelope, and injecting comprises injecting into the silicone containing envelope.

7. The method of claim 6, wherein the implanted medical device comprises an implanted silicone breast implant comprising the at least one silicone containing envelope, and the predetermined volume of the injectable composition comprises a volume of from about 50 ml to about 800 ml.

8. The method of claim 5, wherein the implanted medical device comprises an unfilled or partially filled tissue expander or an unfilled or partially filled lumpectomy implant.

9. The method of claim 5, wherein the implanted medical device comprises an adjustable breast implant comprising an unfilled first envelope and a second envelope comprising a silicone gel.

10. The method of claim 9, wherein injecting comprises injecting the volume into the first unfilled envelope and/or the second envelope.

11. The method of claim 5, wherein the implanted medical device comprises a silicone filled breast implant comprising a shell having an upper pole wrinkling defect and/or lower pole wrinkling defect.

12. The method of claim 11, wherein injecting comprises injecting a volume of the rapidly cross-linkable silicone composition into the upper pole and/or the lower pole of the shell at a site of wrinkling, wherein the volume is sufficient to fill the shell to capacity, whereby the wrinkling defect is ameliorated or eliminated.

13. A method of adjusting the volume of an implanted medical device in situ, comprising:
   providing a dual syringe hypodermic device comprising:
      a static mixer including a first syringe containing a catalyst fluid, a second syringe containing a cross-linker fluid, and an 18 to 21 gauge hypodermic needle, the static mixer configured to mix and inject the catalyst fluid and the cross-linker fluid substantially simultaneously at point of use;
      the catalyst fluid comprising
         a first low viscosity vinyl terminated polydimethylsiloxane present in an amount of from about 97 wt % to about 99.5 wt % based on the weight of the catalyst fluid and having a viscosity of from about 1 to about 150 cPs, and
         a platinum divinyl disiloxane complex comprising Pt[(CH2=CH)(CH3)2SiOSi(CH3)2(CH=CH2)]3 having a platinum content of from about 2 ppm to about 32 ppm based on the catalyst fluid,
      wherein the catalyst fluid has a viscosity of from about 1 to about 150; and
      the cross-linker fluid comprising
         a second low viscosity vinyl terminated polydimethylsiloxane present in an amount of from about 1 wt % to about 40 wt % based on the weight of the cross-linker fluid and having a viscosity of from about 1 to about 150 cPs,
         a low viscosity hydride terminated polydimethylsiloxane present in an amount of from about 60 wt % to about 90 wt % based on the weight of the cross-linker fluid and having a viscosity of from about 1 to about 150 cPs, and a silicone cross-linker comprising polymethylhydrosiloxane polydimethylsiloxane copolymer present in an amount of from about 0.32 wt % to about 5.0 wt % based on the weight of the cross-linker fluid, and having a viscosity of from about 1 to about 150 cPs, wherein the cross-linker fluid has a viscosity of from about 1 to about 150 cPs, and wherein post-preparation or post-mixing of the catalyst fluid and the cross-linker fluid, a resultant rapidly cross-linkable silicone composition has a viscosity of ≤150 cPs for ≥1 min. post-preparation and ≤300 cPs≤5 min. post-preparation, at ambient temperature, and the resultant rapidly cross-linkable silicone composition has a platinum content of from about 1 ppm to about 16 ppm;

mixing the catalyst fluid with the cross-linker fluid via the static mixer to produce an injectable composition having an initial viscosity of <150 cPs for at least about 1 min.; and within ≤5 min. of initiating mixing, and substantially simultaneous with mixing, injecting a predetermined volume of the injectable composition via the dual syringe hypodermic device, into the implanted medical device in situ, whereby the rapidly cross-linkable silicone composition substantially cross-links and gels in situ in an amount of time ≥5 min. to produce a filled implant comprising a homogeneous silicone gel, wherein the rapidly cross-linkable silicone gel has a viscosity ≥50,000 cPs≤24 hrs. post-injection at ambient temperature, and the volume of the implanted device has been adjusted.

14. The method of claim 13, wherein the implanted device comprises an adjustable breast implant comprising an unfilled first envelope and a second envelope comprising a silicone gel, and injecting comprises injecting the volume into the first unfilled envelope and/or the second envelope.

15. The method of claim 1, wherein initiating mixing and injecting are carried out substantially simultaneously.

* * * * *